United States Patent
Hoshino et al.

(10) Patent No.: US 6,936,220 B2
(45) Date of Patent: Aug. 30, 2005

(54) DISINFECTING AND DEODORIZING AGENT

(75) Inventors: Eiichi Hoshino, Tochigi (JP);
Yoshifumi Niki, Tochigi (JP); Koji Hanaoka, Tochigi (JP); Hironobu Sionome, Tochigi (JP)

(73) Assignee: Kao Corporation, Tokyo (JP)

( * ) Notice: Subject to any disclaimer, the term of this patent is extended or adjusted under 35 U.S.C. 154(b) by 595 days.

(21) Appl. No.: 10/149,967

(22) PCT Filed: Apr. 16, 2001

(86) PCT No.: PCT/JP01/03236
§ 371 (c)(1),
(2), (4) Date: Jun. 18, 2002

(87) PCT Pub. No.: WO01/84932
PCT Pub. Date: Nov. 15, 2001

(65) Prior Publication Data
US 2002/0179884 A1 Dec. 5, 2002

(51) Int. Cl.⁷ .................................................. A61L 2/00
(52) U.S. Cl. ...................................... 422/28; 252/186.3
(58) Field of Search .......................... 422/40; 252/186.3

(56) References Cited

U.S. PATENT DOCUMENTS 6,436,342 B1 * 8/2002 Petri et al. ..................... 422/28
6,475,970 B1 * 11/2002 Del Duca et al. ............ 510/375
2002/0098159 A1 * 7/2002 Wei et al. ................... 424/70.1

FOREIGN PATENT DOCUMENTS

| EP | 0 424 845 A2 | 5/1991 |
|----|--------------|--------|
| JP | 2-56406 A | 2/1990 |
| JP | 10-316517 A | 12/1998 |
| JP | 11-236595 A | 8/1999 |
| JP | 2001-151609 A | 6/2001 |

* cited by examiner

Primary Examiner—John Kim
Assistant Examiner—Brad Y. Chinn
(74) Attorney, Agent, or Firm—Birch, Stewart, Kolasch & Birch, LLP

(57) ABSTRACT

A disinfecting deodorant comprising an aqueous solution containing 10 to 1000 ppm of a chlorine-containing oxidizing agent and having a pH adjusted to 8 to 13 with an inorganic salt or an organic salt, a disinfecting and deodorizing method comprising applying the disinfecting deodorant to air or an object, and a disinfecting and deodorizing tool comprising a container having the disinfecting deodorant, the container being equipped with a prescribed atomizing means designed to atomize the disinfecting deodorant into a mist comprising droplets having a particle size of 10 μm or smaller in a proportion of 2% or less in number in a particle frequency distribution.

3 Claims, No Drawings

DISINFECTING AND DEODORIZING AGENT

This application is the national phase under 35 U.S.C. §371 of PCT International Application No. PCT/JP01/03236 which has an International filing date of Apr. 16, 2001, which designated the United States of America.

TECHNICAL FIELD

The present invention relates to a disinfecting deodorant and a disinfecting and deodorizing method which are effective for disinfecting and/or deodorizing an object or a space.

BACKGROUND ART

An aqueous solution containing a chlorine compound such as a hypochlorite (e.g., an alkali metal hypochlorite) in a several to ten-odd percent concentration and, as an alkali agent, an alkali metal hydroxide, etc., e.g., sodium hydroxide, is known as an effective disinfecting deodorant. For example, JP-A-11-236595 discloses a composition comprising 3 wt % sodium hypochlorite, 1 wt % sodium hydroxide, and 1 wt % polyoxyethylene lauryl alcohol.

Having the chlorine compound in a high concentration, such a disinfecting deodorant exerts excellent disinfecting and deodorizing effects but has limited applicability in place or usage because of its liability to damage objects (decoloration or discoloration of colored or patterned clothing and deterioration or damage of metal, plastics, wood, etc.) and, in some cases, from the standpoint of safety. For instance it is unfit for spraying in a space, such as a room, for the purpose of deodorizing.

Reduction in concentration of the chlorine compound in an attempt to ensure safety and prevent damage to objects has involve difficulties in obtaining a formulation with satisfactory storage stability. That is, the activity would be reduced considerably due to the surrounding temperature, light (ultraviolet light), a third component adhered to a container, etc., a pigment present in a container material, and so on, and chlorine gas can generate with decomposition of the chlorine compound. Thus, it has been difficult with a disinfecting deodorant comprising an aqueous solution of the chlorine compound to achieve sufficient disinfecting and deodorizing effects in such a low concentration range as to satisfy requirements for safety and the like.

DISCLOSURE OF THE INVENTION

Accordingly, an object of the present invention is to provide a disinfecting deodorant and a disinfecting and deodorizing method, in which a chlorine compound produces sufficient effects in such a low concentration range as to ensure safety and not to damage objects.

As a result of extensive investigation, the present inventors have found that a disinfecting deodorant containing a chlorine compound in a specific low concentration and having a specific pH satisfies all the requirements for safety, non-damaging properties, storage stability, and disinfecting and deodorizing effects. They have also found that sufficient disinfecting and deodorizing effects can be exerted by spraying an object or a space with such a thin aqueous solution.

The present invention has been completed based on the above findings. The invention has accomplished the objects by providing a disinfecting deodorant comprising an aqueous solution containing 10 to 1000 ppm of a chlorine-containing oxidizing agent and having a pH adjusted to 8 to 13 with an inorganic salt or an organic salt.

The invention has also accomplished the objects by providing a disinfecting and deodorizing method comprising applying an aqueous solution containing 10 to 1000 ppm of a chlorine-containing oxidizing agent and having a pH adjusted to 8 to 13 with an inorganic or organic salt to air or an object by a prescribed means.

The present invention also provides a disinfecting and deodorizing tool comprising a container having an aqueous solution containing 10 to 1000 ppm of a chlorine-containing oxidizing agent and having a pH adjusted to 8 to 13 with an inorganic salt or an organic salt, the container being equipped with a prescribed atomizing means designed to atomize the aqueous solution into a mist comprising droplets having a particle size of 10 $\mu$m or smaller in a proportion of 2% or less in number in a particle frequency distribution.

BEST MODE FOR CARRYING OUT THE INVENTION

The present invention will be described with reference to its preferred embodiments. The disinfecting deodorant of the present invention comprises an aqueous solution containing a chlorine-containing oxidizing agent. The chlorine-containing oxidizing agent is selected from components effective in disinfecting and/or deodorizing an object or a space to be disinfected and/or deodorized, including hypochlorites, dichloroisocyanurates, trichloroisocyanurates, chlorinated lime (high granules), dichloromethyl hydantoin, bromochlorodimethyl hydantoin, and calcium chlorite. Preferred of them are alkali metal hypochlorites, such as sodium hypochlorite and potassium hypochlorite, from the standpoint of cost, oxidizing power, and stability.

The chlorine-containing oxidizing agent is used in a concentration of 10 to 1000 ppm (=mg/kg), preferably 50 to 500 ppm, still preferably 80 to 200 ppm. This concentration range is extremely much lower than those of conventional disinfecting deodorants containing chlorine-containing oxidizing agent. In concentrations exceeding 1000 ppm, the oxidizing agent causes decoloration or discoloration of colored or patterned clothing, bedding, curtains, etc.; deterioration or damage of metal, plastics, wood, etc., and, in some cases, has a question as to safety when sprayed, having a possibility of irritating the eye mucosa. In concentrations lower than 10 ppm, the oxidizing agent fails to exhibit sufficient disinfecting and/or deodorizing effects on an object or in a space. It is difficult for a formulation having such a low concentration to have sufficient storage stability because of susceptibility to influences of other ingredients in the formulation, third components adhered to the container, etc., pigments contained in the container material, the surrounding temperature, ultraviolet light, and so forth. The chlorine-containing oxidizing agent is used in the form an aqueous solution. The concentration in the aqueous solution is 10 to 1000 ppm as recited above. The pH of the aqueous solution is 8 to 13 as described below.

The disinfecting deodorant according to the present invention has a pH adjusted to 8 to 13, preferably 9 to 12, still preferably 9.5 to 11, with an inorganic salt or an organic salt. It the pH is below 8, the disinfecting deodorant has a fear of generating chlorine gas with decomposition of the chlorine-containing oxidizing agent and fails to have sufficient storage stability. A pH exceeding 13 damages an object and, in some cases, has a question as to safety, and can fail to produce sufficient deodorizing and disinfecting effects.

The inorganic salt or organic salt to be used is selected from those having a buffering action capable of stably adjusting the pH of the disinfecting deodorant of the present invention within the above-described range. Preferred are those having low reactivity with the chlorine-containing oxidizing agent so as not to impair the stability of the chlorine-containing oxidizing agent. Seeing that the inorganic salt or the organic salt is required to have a buffering action for adjusting the pH of the disinfecting deodorant of the invention within the above range in a stable manner, it is particularly desirable for the inorganic salt or the organic salt to have a pKa value at 25° C. (hereinafter referred to as $pKa_{25}$) of 7 or greater, preferably 7 to 12.5, still preferably 8 to 12.5, still preferably 9 to 11.

The inorganic salt includes alkali metal phosphates, such as potassium phosphate, dipotassium hydrogenphosphate, and potassium dihydrogenphosphate; alkali metal pyrophosphates, such as sodium pyrophosphate and trisodium hydrogen pyrophosphate; alkali metal tripolyphosphates, such as sodium tripolyphosphate; alkali metal carbonates, such as sodium carbonate and sodium hydrogencarbonate; and alkali metal borates such as borax. The organic salt includes alkali metal aspartates, such as sodium aspartate; alkali metal ethylenediaminetetraacetates (EDTAs), such as tetrasodium EDTA; glycine hydrochloride, glycylglycine hydrochloride, triethanolamine hydrochloride, and ethylenediamine hydrochloride. The inorganic salt or the organic salt is compounded in an amount enough to adjust the disinfecting deodorant of the present invention to a pH within the above range and to be allowed to exert a buffering action within that pH range.

If desired, the disinfecting deodorant of the present invention may contain additional ingredients, such as various surface active agents, alkali agents (e.g., sodium hydroxide), chelating agents, solvents, thickeners, perfumes, and the like. The kinds and amounts of these ingredients are decided so as not to ruin the stability of the chlorine-containing oxidizing agent.

Water is a medium of the disinfecting deodorant of the invention, taking the balance other than the total amount of the aforementioned ingredients.

The disinfecting deodorant of the present invention has disinfecting and antimicrobial actions on various fungi, such as mold, and various bacteria, such as *E. coli* and *Staph. aureaus,* to keep an object or a space clean and suppress generation of bad odors. The disinfecting deodorant of the invention exerts its effect in disinfecting and deodorizing a smelling space, a cutting board and dusters in a kitchen, a dining table, etc.; removing a musty smell of a storeroom or cushions; disinfecting and deodorizing shoe storage furniture; disinfecting and deodorizing a toilet; and decomposing and deodorizing a variety of bad odors, such as the odors clinging to bedding, clothing, carpets, tatami mats, curtains, etc. (e.g., the odor of sebum, the body odor inherent to the elderly, and the odor of tobacco), the odor of pet animals, and the body waste odor of used disposable diapers or a bag for putting used disposable diapers in. For example, the disinfecting deodorant of the present invention is applied in the form of a mist on bedding or clothing of a care-receiver, a newborn baby or an infant, especially such a care-receiver as a bedridden elderly person, or to air in his or her living space thereby to remove the bad odors and to achieve disinfection. Unlike conventional deodorants of the type which mask bad odors by perfuming, the disinfecting deodorant of the present invention does not make an unpleasant mixture of a fragrance and a bad odor. In addition, the smell of the disinfecting deodorant of the present invention suggests hygiene and gives a user a good impression.

The disinfecting deodorant of the present invention manifests its disinfecting and deodorizing effects when applied to air or an object by a prescribed means. The disinfecting deodorant of the present invention is preferably applied by spraying or coating. Spraying is particularly convenient. Where the disinfecting deodorant of the invention is sprayed in a space or onto an object, useful spraying methods include a method making use of an air pressure, such as various trigger sprayers, a method using a vibrator, e.g., an ultrasonic vibrator, and a method by heating.

Where the disinfecting deodorant of the present invention is applied by spraying, it is preferred to atomize the disinfecting deodorant into a mist comprising droplets having a particle size of 10 μm or smaller in a proportion of 2% or less in number in a particle frequency distribution. This is favorable for avoiding very fine droplets of the disinfecting deodorant being suspended in air for a long time, which will lead to enhanced safety. While the particle frequency distribution of the other droplets is not particularly restricted, it is advisable to control the liquid particle sizes so that a spray onto an object or into a space may not wet the object, the floor, etc. to leave stains or cause a slip.

The liquid particle size is measured with, for example, a laser diffraction particle size analyzer (Particle Size Analyzer, supplied by JEOL Ltd.). The disinfecting deodorant of the invention can be made into a misty state having the above-described particle size distribution by putting it in a container equipped with a prescribed atomizing means and atomizing it into a space or onto an object with that means. As an atomizing means, a means making use of an air pressure, such as various trigger sprayers, is preferred in view of portability, ease of handling, resistance to corrosion by the chlorine-containing oxidizing agent, ease of particle size control, ease of disposing of a used container, and the like.

EXAMPLES

The present invention will now be illustrated in greater detail with reference to Examples. Unless otherwise noted, all the percents and parts are given by weight.

Example 1 and Comparative Example 1

A 35 mm-diameter disc of plain weave cotton cloth dyed in red (basis weight: 140 g/m$^2$) was impregnated with 100 μl of a 1% ethanolic solution of 1-octen-3-ol to make a musky odor model. The cotton cloth piece was sealed into a 1.8 liter closed glass container with a lid at 20° C. and 65% RH. A disinfecting deodorant comprising an aqueous solution containing 100 ppm of sodium hypochlorite and 0.5% of dipotassium hydrogenphosphate ($pKa_{25}$=12.38) and having a pH adjusted to 9.3 was put in a plastic container having a trigger sprayer. The lid of the glass container was opened, 0.5 g of mist of the disinfecting deodorant was applied to the cotton cloth, and the lid was closed again. The number of droplets having a particle size of 10 μm or smaller in the mist was 0.85% in a frequency distribution (Example 1). As a control, distilled water was put in the same plastic container in place of the disinfecting deodorant and sprayed in the same amount (Comparative Example 1).

The cotton cloth was smelled by a panel of 5 members before being sprayed or after 5 minutes from spraying with the disinfecting deodorant or water. The intensity of the odor was evaluated based on the following scoring system. An average score was calculated. The smaller the average score, the weaker the smell.

0 . . . Odorless
1 . . . Barely perceptible odor
2 . . . Identifiable odor
3 . . . Easily perceptible odor
4 . . . Strong odor
5 . . . Unbearably strong odor As a result of evaluation, the intensity of odor before spraying was 4 but reduced to 0.8 after spraying with the disinfecting deodorant (Example 1). The odor after spraying with water (Comparative Example 1) was 3.1.

The color of the cotton cloth piece sprayed with the disinfecting deodorant or water was measured with a color difference meter. The two cloth pieces were equal in degree of decoloration or discoloration, proving that substantially no decoloration or discoloration occurred. The same test was repeated while changing the color of cotton cloth to blue, yellow, green, black, gray, brown or pink to give the same results.

Example 2 and Comparative Example 2

A disposable diaper after use was collected, and a 5 g portion was taken out of the absorbent member having absorbed urine. The portion was sealed into a 1.8 liter glass container with a lid at 20° C. and 65% RH in the same manner as in Example 1. A disinfecting deodorant comprising an aqueous solution containing 80 ppm of sodium hypochlorite and 0.5% of dipotassium hydrogenphosphate and further having added thereto a prescribed amount of a 2% aqueous solution of sodium hydroxide as an alkali agent to adjust to a final pH of 10.5 was put in the same plastic container with a trigger sprayer as used in Example 1. The lid of the glass container was opened, 0.5 g of mist of the disinfecting deodorant was sprayed in the container, and the lid was closed again. The number of droplets having a particle size of 10 $\mu$m or smaller in the mist was 0.91% in a frequency distribution (Example 2). As a control, distilled water was put in the plastic container in place of the disinfecting deodorant and sprayed in the same amount (Comparative Example 2).

A panel smelled the diaper before spraying or after 5 minutes from spraying with the disinfecting deodorant or water and rated the intensity of the smell in the same manner as in Example 1. As a result, the odor before spraying was 5 but reduced to 0.7 after spraying with the disinfecting deodorant (Example 2). The odor after spraying with water (Comparative Example 2) was 3.8.

The chlorine gas concentration in the glass container where the diaper sprayed with the disinfecting deodorant had been placed was measured with a gas detector tube and was found below the detectable limit (0.1 ppm).

Example 3 and Comparative Example 3

The same cotton cloth piece as used in Example 1 was impregnated with 20 $\mu$m of a 0.01% solution of isovaleric acid in diethylene glycol as a model body odor of the elderly and pet animals and sealed in a closed glass container with a lid in the same manner as in Example 1. A disinfecting deodorant comprising an aqueous solution containing 150 ppm of sodium hypochlorite and 0.5% of dipotassium hydrogenphosphate and further having added thereto a prescribed amount of a 2% aqueous solution of sodium hydroxide as an alkali agent to adjust to a final pH of 10.0 was put in the same plastic container as used in Example 1. The lid of the glass container was opened, and 0.5 g of mist of the disinfecting deodorant was sprayed to the cotton cloth. The number of droplets having a particle size of 10 $\mu$m or smaller in the mist was 0.89% in a frequency distribution (Example 3). As a control, distilled water was put in the plastic container in place of the disinfecting deodorant and sprayed in the same amount (Comparative Example 3).

The odor of the cotton cloth was smelled before spraying and after 5 minutes from spraying with the disinfecting deodorant or water and rated in the same manner as in Example 1. As a result, the odor before spraying was 3 but reduced to 0.2 after spraying with the disinfecting deodorant (Example 3). The odor after spraying with water (Comparative Example 3) was 2.3.

Example 4 and Comparative Example 4

A piece of cattle leather for shoes weighing 3 g and having a water content of 30% was sealed in a closed glass container with a lid in the same manner as in Example 1. A disinfecting deodorant comprising an aqueous solution containing 200 ppm of sodium hypochlorite and 0.5% of dipotassium hydrogenphosphate and further having added thereto a prescribed amount of a 2% aqueous solution of sodium hydroxide as an alkali agent to adjust to a final pH of 10.9 was put in the same plastic container as used in Example 1. The lid of the glass container was opened, and 1.0 g of mist of the disinfecting deodorant was sprayed to the cattle leather. The sprayed cattle leather was allowed to stand at 30° C. for 5 days (Example 4). As a control, distilled water was put in the plastic container in place of the disinfecting deodorant and sprayed in the same amount. The sprayed cattle leather was allowed to stand under the same conditions (Comparative Example 4).

After the 5 day standing, no mold was found growing on the cattle leather sprayed with the disinfecting deodorant (Example 4), whereas the cattle leather sprayed with distill water gathered much mold (Comparative Example 4).

Example 5 and Comparative Example 5

A disinfecting deodorant comprising an aqueous solution containing 80 ppm of sodium hypochlorite and 0.5% of sodium tetraborate ($pKa_{25}$=9.24) and further having added thereto a prescribed amount of a 2% aqueous solution of sodium hydroxide as an alkali agent to adjust to a final pH of 10.5 was put in the same plastic container with a trigger sprayer as used in Example 1. A glass container having put therein a piece of an absorbent member of a used disposable diaper was prepared in the same manner as in Example 1. The lid of the container was opened, 0.5 g of mist of the disinfecting deodorant was sprayed, and the lid was closed again. The number of droplets having a particle size of 10 $\mu$m or smaller in the mist was 0.90% in a frequency distribution (Example 5). As a control, distilled water was put in the plastic container in place of the disinfecting deodorant and sprayed in the same amount (Comparative Example 5).

A panel smelled the diaper before spraying and after 5 minutes from spraying with the disinfecting deodorant or water and rated the intensity of the smell in the same manner as in Example 1. As a result, the odor before spraying was 5 but reduced to 0.5 after spraying with the disinfecting deodorant (Example 5). The odor after spraying with water (Comparative Example 5) was 3.8.

Examples 6 to 8 and Comparative Example 6

A disinfecting deodorant comprising an aqueous solution containing 200 ppm of sodium hypochlorite and 0.5% of sodium hydrogencarbonate ($pKa_{25}$=10.33) and further having added thereto a prescribed amount of a 2% aqueous solution of sodium hydroxide as an alkali agent to adjust to a final pH of 10.5 was put in the same plastic container with a trigger sprayer as used in Example 1 (Example 6). When a 0.5 g portion of the disinfecting deodorant was sprayed, the number of droplets having a particle size of 10 μm or smaller in the mist was 0.88% in a frequency distribution.

A disinfecting deodorant (pH=10.5) was prepared in the same manner as in Example 6, except that the sodium hydrogencarbonate used in Example 6 was replaced with trisodium pyrophosphate ($pKa_{25}$=8.95). The resulting disinfecting deodorant was put in the same plastic container with a trigger sprayer as used in Example 1 (Example 7). When a 0.5 g portion of the disinfecting deodorant was sprayed, the number of droplets having a particle size of 10 μm or smaller in the mist was 0.89% in a frequency distribution.

A disinfecting deodorant was prepared in the same manner as in Example 7, except that the trisodium pyrophosphate used in Example 7 was replaced with sodium tripolyphosphate ($pKa_{25}$=9.70), and was put in the same plastic container with a trigger sprayer as used in Example 1 (Example 8). When a 0.5 g portion of the disinfecting deodorant was sprayed, the number of droplets having a particle size of 10 μm or smaller in the mist was 0.87% in a frequency distribution.

An aqueous solution containing 200 ppm of sodium hypochlorite and having added thereto a prescribed amount of a 2% aqueous solution of sodium hydroxide to adjust to a pH of 10.5 was put in the same plastic container with a trigger sprayer as used in Example 1 (Comparative Example 6). When a 0.5 g portion of the resulting disinfecting deodorant was sprayed, the number of droplets having a particle size of 10 μm or smaller in the mist was 0.88% in a frequency distribution.

The disinfecting deodorants of Examples 6, 7, and 8 and Comparative Example 6 were allowed to stand in a constant temperature room set at 40° C. for 3 months and then tested for deodorizing performance on a used disposable diaper in the same manner as in Example 2. A panel smelled the diaper before spraying and after 5 minutes from spraying with each disinfecting deodorant and rated the intensity of the smell in the same manner as in Example 1. As a result, the odor before spraying was 5 but reduced to 0.6. 0.8 or 0.7 after spraying with the disinfecting deodorant of Example 6, 7 or 8, respectively. In Comparative Example 6, the odor was 4.0.

INDUSTRIAL APPLICABILITY

The present invention provides a disinfecting deodorant and a disinfecting and deodorizing method which achieve sufficient effects at a low chlorine compound concentration range while eliminating damage to a treated object and ensuring safety.

What is claimed is:

1. A disinfecting and deodorizing method comprising applying an aqueous solution to air or an object by a prescribed means in the form of a mist comprising droplets having a particle size of 10 μm or smaller in a proportion of 2% or less in number in a particle frequency distribution, said aqueous solution containing 10 to 1000 ppm of a chlorine-containing oxidizing agent and having a pH adjusted to 8 to 13 with an inorganic salt or an organic salt.

2. The disinfecting and deodorizing method according to claim 1, wherein said aqueous solution is sprayed to the bedding and clothing of a care-receiver, a newborn baby or an infant or air in his or her living space.

3. A disinfecting and deodorizing tool comprising a container having an aqueous solution containing 10 to 1000 ppm of a chlorine-containing oxidizing agent and having a pH adjusted to 8 to 13 with an inorganic salt or an organic salt, said container being equipped with a prescribed atomizing means designed to atomize said aqueous solution into a mist comprising droplets having a particle size of 10 μm or smaller in a proportion of 2% or less in number in a particle frequency distribution.

* * * * *

UNITED STATES PATENT AND TRADEMARK OFFICE
CERTIFICATE OF CORRECTION

PATENT NO.          : 6,936,220 B2                                        Page 1 of 1
APPLICATION NO.  : 10/149967
DATED                  : August 30, 2005
INVENTOR(S)         : Eiichi Hoshino et al.

It is certified that error appears in the above-identified patent and that said Letters Patent is hereby corrected as shown below:

Title page    --Foreign Application Priority Data
JAPAN 2000-136667 May 10, 2000--

Signed and Sealed this

Eleventh Day of July, 2006

JON W. DUDAS
*Director of the United States Patent and Trademark Office*